United States Patent [19]

Thiem et al.

[11] 3,933,867

[45] Jan. 20, 1976

[54] PROCESS FOR THE PREPARATION OF 1-AMINOANTHRAQUINONE

[75] Inventors: Karl-Werner Thiem, Cologne; Wolfgang Auge, Odenthal; Rutger Neeff, Leverkusen, all of Germany

[73] Assignee: Bayer Aktiengesellschaft, Leverkusen Bayerwerk, Germany

[22] Filed: Mar. 22, 1974

[21] Appl. No.: 453,971

[30] Foreign Application Priority Data

Mar. 22, 1973 Germany............................ 2314218

[52] U.S. Cl. ................................................. 260/382
[51] Int. Cl.² ........................................ C07C 97/24
[58] Field of Search....... 260/382, 378, 580, 583 M,

260/689

[56] References Cited
FOREIGN PATENTS OR APPLICATIONS 2,211,411  9/1972  Germany ............................ 260/382

Primary Examiner—Richard L. Raymond
Attorney, Agent, or Firm—Plumley & Tyner

[57] ABSTRACT

Process for the preparation of 1-aminoanthraquinone by reaction of 1-nitroanthraquinone with ammonia in organic solvents, characterised in that the reaction is carried out in ethers, aliphatic or cycloaliphatic hydrocarbons or optionally alkyl-substituted aromatic hydrocarbons.

6 Claims, No Drawings

PROCESS FOR THE PREPARATION OF 1-AMINOANTHRAQUINONE

German Offenlegungsschrift (German Published Specification) 2,211,411 describes a process for the preparation of aminoanthraquinones according to which aminoanthraquinones are obtained from nitroanthraquinones by reaction with ammonia, ammonium salts or amides in the presence of an amide which is liquid under the reaction conditions. The reaction is carried out at an elevated temperature, preferably between 100° and 180°C, and optionally under pressure. The amides used are low molecular organic amides, for example formamide, urea or N-methylpyrrolidone.

The reaction mixture is worked up according to methods which are in themselves known, for example by distilling off the amide or by precipitating the aminoanthraquinone with water, or by extraction.

However, if the process is carried out under the conditions stated in this Offenlegungsschrift (Published Specification), it is found that the 1-aminoanthraquinone formed is not stable under the reaction conditions used and that several undesired by-products are formed.

The 1-aminoanthraquinone thus obtained is, however, not pure enough for further conversion to dyestuffs (Example 8).

It has now been found that purer 1-aminoanthraquinone is obtained if 1-nitroanthraquinone, in ethers, aliphatic and cycloaliphatic hydrocarbons, optionally alkyl-substituted aromatic hydrocarbons or mixtures of these solvents, is reacted with ammonia, preferably under pressure and at elevated temperature.

The 1-aminoanthraquinone thus prepared can be further converted to dyestuffs without additional purification, for example purification by distillation.

Suitable ethers are, in particular, aliphatic, cycloaliphatic and aromatic ethers, such as dibenzyl ether, di-sec.-butyl ether, diisopentyl ether, ethylene glycol dimethyl ether, diethylene glycol dimethyl ether, diethylene glycol diethyl ether, methoxycyclohexane, ethoxycyclohexane, dicyclohexyl ether, anisole, phenetole, diphenyl ether, 2-methoxynaphthalene, tetrahydrofurane, dioxane, amyl phenyl ether, benzyl isoamyl ether, dibenzyl ether, diglycol di-n-butyl ether, glycol methylene ether and methyl benzyl ether.

Examples of suitable aliphatic and cycloaliphatic hydrocarbons are n-pentane, n-hexane, n-heptane, cyclohexane, methylcyclohexane, cyclododecane, decalin, cycloheptane, cyclopentane, n-decane, 1,2-dimethylcyclohexane, 1,3-dimethylcyclohexane, 1,4-dimethylcyclohexane, 2,2-dimethylpentane, 2,3-dimethylpentane, 2,4-dimethylpentane, 3,3-dimethylpentane, isopropylhexane, methylcyclohexane, 2-methylheptane, 3-methylheptane, 4-methylheptane, 2-methylhexane, 3-methylhexane, 2-methyloctane, 3-methyloctane, 4-methyloctane, 2-methylpentane, 3-methylpentane, n-octane, pentaisobutane, triethylmethane, 2,2,3-trimethylpentane, 2,2,4-trimethylpentane and 2,3,3-trimethylpentane.

Examples of suitable aromatic hydrocarbons are benzene, toluene, o-, m- and p-xylene, isopropylbenzene, trimethylbenzene, diethylbenzene, tetramethylbenzene, di-isopropylbenzene, isododecylbenzene, tetralin, naphthalene, methylnaphthalene, diphenyl, diphenylmethane, o-, m- and p-cymene, dibenzyl, dihydronephthalene, 2,2'-dimethyl-diphenyl, 2,3'-dimethyldiphenyl, 2,4'-dimethyl-diphenyl, 3,3'-dimethyldiphenyl, 1,2-dimethylnaphthalene, 1,4-dimethylnaphthalene, 1,6-dimethylnaphthalene, 1,7-dimethylnaphthalene, 1,1-diphenylethane, hexamethylbenzene, isoamylbenzene, pentamethylbenzene, 1,2,3,4-tetramethylbenzene, 1,2,3,5-tetramethylbenzene, 1,2,7-trimethylnaphthalene and 1,2,5-trimethylnaphthalene.

In detail, the process according to the invention is carried out, for example, as follows: at temperatures of 100°–220°C, preferably 140°–200°, and at molar ratios (by molar ratio there is to be understood, here and in the following text, the molar ratio of ammonia to 1-nitroanthraquinone) of at least 2:1, preferably 10:1 to 40:1 and in particular 15:1 to 35:1. The reaction is in general carried out under pressure, expecially >20 atmospheres and preferably >50 atmospheres.

The reaction time depends on the temperature, the pressure and the molar ratio and in particular the reaction velocity increases with increasing temperature, increasing molar ratio and increasing pressure. For example, if a molar ratio of 10:1 is used at 200°C (150° or 130°C) and at approx. 100 atmospheres, the reaction is complete after 0.5 (3 or 5) hours, whilst, for example, at a molar ratio of 50:1 and a temperature of 100°C (30:1 at 130°C or 20:1 at 150°C) and at >100 atmospheres a reaction time of less than 5 hours (less than 4 or less than 0.5 hours, respectively) is to be expected.

The process can be carried out continuously or discontinuously.

The reaction mixture can be worked up according to customary methods, for example by filtering off the product which crystallises out from the organic solvent after cooling to room temperature. The mother liquor which arises at the same time can be recycled to the process.

The working up of the reaction mixture can, however, also be effected by distilling off the solvent or by precipitating the 1-aminoanthraquinone with the aid of a diluent which lowers the solubility of the 1-aminoanthraquinone in the reaction solution (for example petroleum ether). If necessary, the reaction product can be purified further by treatment with acids, for example sulphuric acid.

Accordingly, the subject of the present invention is a process for the preparation of pure 1-aminoanthraquinone which is characterised in that 1-nitroanthraquinone, in ethers, aliphatic and cycloaliphatic hydrocarbons, optionally alkyl-substituted aromatic hydrocarbons or mixtures of these compounds, is reacted with ammonia, preferably under pressure, especially at pressures of >20 and preferably >50 atmospheres, and at molar ratios of ammonia to 1-nitroanthraquinone of at least 2:1, especially of 10:1 and preferably of 15:1 to 35:1, at elevated temperature, preferably at 100° – 220°C and especially at 140° – 200°C. The process according to the invention is also suitable for the preparation of pure 1-aminoanthraquinone from mixtures of 1-nitroanthraquinone and 2-nitroanthraquinone, such as are obtained, for example, from the nitration of anthraquinone, after separating off the dinitroanthraquinones. This is because the process according to the invention results very preferentially in reaction of the nitro group in the 1-position; if the reaction is stopped after complete conversion of the 1-nitroanthraquinone, a mixture of 1-aminoanthraquinone and 2-nitroanthraquinone is obtained, which can be separated easily.

One possibility is, for example, to dissolve the mixture in acids such as, for example, sulphuric acid, then to precipitate the 2-nitroanthraquinone first by dilution of the acid with water (for example 50–70% strength sulphuric acid) and separate it off, and subsequently to precipitate the 1-aminoanthraquinone from the filtrate by further dilution, and isolate it.

A further possibility is, for example, to convert the 1-aminoanthraquinone into α-thionyl-aminoanthraquinone (U.S. Pat. No. 2,479,943), which is readily soluble in organic solvents, such as, for example, benzene or toluene, in which case the sparingly soluble 2-nitroanthraquinone can be separated off.

Hence, a further subject of the present invention is a process for the preparation of 1-aminoanthraquinone which is essentially free of 2-nitroanthraquinone, from mixtures which contain 1-nitroanthraquinone and 2-nitroanthraquinone, characterised in that the mixture, in ethers, aliphatic or cycloaliphatic hydrocarbons, optionally alkyl-substituted aromatic hydrocarbons or mixtures of these compounds, is reacted with ammonia, preferably under pressure, especially at not less than 20 and preferably at not less than 50 atmospheres, and that a molar ratio of ammonia to 1-nitroanthraquinone of at least 2:1, especially 10:1 to 40:1 and preferably 15:1 to 35:1, at an elevated temperature, preferably at 100° – 220°C and especially at 140° – 200°C, until the 1-nitroanthraquinone has been completely converted, and that the reaction product is subsequently separated into 1-aminoanthraquinone and 2-nitroanthraquinone.

As compared to the process known from German Offenlegungsschrift (German Published Specification) 2,211,411, the process according to the invention has the advantage that the organic solvents claimed do not participate in the reaction and that practically no undesired by-products are formed. The 1-aminoanthraquinone thus obtained can accordingly be further converted to dyestuffs without having to carry out additional purification operations.

EXAMPLE 1

A mixture of 257 g of 1-nitroanthraquinone (98.5% pure) and 1 liter of toluene is reacted with 340 g of ammonia in an autoclave (~100 atmospheres) for ¼ hour at 170°C (molar ratio 20:1).

After cooling to room temperature, the reaction mixture is filtered and the residue is washed with a little toluene and dried in vacuo. Yield: 224 g of a 97% pure 1-aminoanthraquinone (97% of theory).

Similar yields and purities result if instead of toluene, benzene, 1,3,5-trimethylbenzene, isopropylbenzene, isododecylbenzene, diphenylmethane, n-hexane, n-heptane, decalin, tetralin, methylcyclohexane, cyclododecane, n-dipropyl ether, dibutyl ether, diethylene glycol dimethyl ether, diethylene glycol diethyl ether, methoxycyclohexane, dicyclohexyl ether, anisole, phenetole, diphenyl ether, tetrahydrofurane, dioxane or mixtures of these solvents are used.

EXAMPLE 2

A mixture of 255 g of 1-nitroanthraquinone (99% pure) and 1 liter of cyclohexane is reacted with 51 g of ammonia (molar ratio 3:1) at 180°C in an autoclave (40 atmospheres), using a reaction time of 8 hours. After cooling, and separating off the ammonia, the reaction mixture is extracted by shaking at room temperature with 50 ml of 30% strength sulphuric acid, 100 ml of water are then added and after separation of the phases the mixture is filtered. The residue is washed with a little methanol to remove adhering cyclohexane and is subsequently washed with water until neutral, and dried. Yield: 209 g of 96% pure 1-aminoanthraquinone (90% of theory).

EXAMPLE 3

A mixture of 255 g of 1-nitroanthraquinone (99% pure) and 1 liter of ethylene glycol dimethyl ether is reacted with 510 g of ammonia at ~40 atmospheres (molar ratio 30:1) at 130°C in an autoclave, using a reaction time of 4 hours. After cooling, the reaction mixture is introduced into 5 liters of water and the precipitate formed is filtered off, washed with water and dried. Yield: 217 g of 97.4% pure 1-aminoanthraquinone (95% of theory).

EXAMPLE 4

After reacting 264 g of 1-nitroanthraquinone (96% pure) with 340 g of ammonia (molar ratio 20:1) in 1 liter of n-pentane at 150°C in an autoclave (~100 atmospheres) for 0.5 hour, the resulting reaction mixture is freed from the solvent by distillation. Residue, 220 g of 94.5% pure 1-aminoanthraquinone (93% of theory).

EXAMPLE 5

275 g of 1-nitroanthraquinone (92% pure), containing 7 parts by weight of 2-nitroanthraquinone, in 1.8 liters of toluene, are heated with 255 g of ammonia (molar ratio 15:1) to 180° in an autoclave (~130 atmospheres) for 0.5 hour. The ammonia is removed and the reaction mixture which has cooled is treated with 190 g of thionly chloride according to U.S. Pat. No. 2,479,943, heated for 2 hours under reflux, 10 g of active charcoal are then added and the mixture is filtered hot. 180 ml of methanol are added to the filtrate, the mixture is heated to the boil for 1 hour, the precipitate formed is filtered off at room temperature, the filter cake is suspended in water and the toluene is driven off in steam. The hot suspension is filtered, washed until free of acid and dried. Yield: 209 g of a 97% pure 1-aminoanthraquinone (91% of theory).

EXAMPLE 6

After reacting 275 g of 1-nitroanthraquinone (92% pure; 7% by weight of 2-nitroanthraquinone), in 1 liter of toluene, with 85 g of ammonia (molar ratio 5:1) for 7 hours at 220° in an autoclave (130 atmospheres), the resulting reaction mixture is filtered at room temperature and the residue is dried in vacuo and dissolved in 1 liter of concentrated sulphuric acid. The solution is diluted in the cold to 60% acid content by adding water. After filtering off the precipitate which has separated out, the filtrate is poured out onto ice. The precipitate obtained is filtered off, washed until neutral and dried. Yield, 209 g of a 96% pure 1-aminoanthraquinone (90% of theory).

EXAMPLE 7

A suspension of 264 g/hour of 1-nitroanthraquinone (96% pure) in 2 liters of xylene/hour is continuously reacted in a 3-stage stirred autoclave with 255 g/hour of ammonia (molar ratio 15:1) at 180°C and 100 atmospheres, using a dwell time of 30 minutes. The cooled reaction mixture is continuously filtered at room temperature and the mother liquor is recycled to the process whilst the residue is freed from xylene by means of steam and is then dried. Yield per hour: 220 g of a 94.1% pure 1-aminoanthraquinone (93% of theory).

EXAMPLE 8

German Offenlegungsschrift (German Published Specification) 2,211,411, Example 1.

26.3 g of 1-nitroanthraquinone (96% pure) are suspended in 110 g of formamide. Ammonia gas is passed in at 155°. After 4 hours, the solvent is distilled off and the residue is washed with water. After drying in vacuo, 22.5 g of 70% pure 1-aminoanthraquinone (71% of theory) are obtained.

The 96% pure 1-nitroanthraquinone used was prepared according to German Offenlegungsschrift (German Published Specification) 2,039,822.

We claim:

1. Process for the preparation of 1-aminoanthraquinone comprising reacting at 100°–220°C and superatmospheric pressure 1-nitroanthraquinone with ammonia in a molar ratio of ammonia: 1-nitroanthraquinone of at least 2:1 in at least one organic solvent selected from the group consisting of aliphatic ether, cycloaliphatic ether, aromatic ether, aliphatic hydrocarbon, cycloaliphatic hydrocarbon, aromatic hydrocarbon and alkyl-substituted aromatic hydrocarbon.

2. Process of claim 1 wherein the reaction solvent is an alkylbenzene.

3. Process of claim 1 wherein the reaction is carried out under a pressure greater than 20 atmospheres, and at a molar ratio of ammonia: 1-nitroanthraquinone 10:1 to 40:1.

4. Process of claim 1 wherein the temperature is 140° to 200°C.

5. Process of claim 1 for the preparation of 1-aminoanthraquinone, which is practically free of 2-aminoanthraquinone, from mixtures of 1-nitroanthraquinone and 2-nitroanthraquinone, wherein the mixture in at least one of said organic solvents is reacted with ammonia until the 1-nitroanthraquinone has reacted completely and 1-aminoanthraquinone is then separated from the reaction mixture.

6. Process of claim 3 wherein the pressure is greater than 50 atmospheres and the molar ratio is 15:1 to 35:1.

* * * * *